United States Patent
Chen et al.

(10) Patent No.: US 8,858,615 B2
(45) Date of Patent: Oct. 14, 2014

(54) PREVENTING VASCULAR STENOSIS OF CARDIOVASCULAR STENT

(75) Inventors: Cheng-Shun Chen, Taipei (TW);
Yih-Sharng Chen, Taipei (TW);
Nai-Kuan Chou, Taipei (TW); Hsi-Yu Yu, Taipei (TW); Sheng-Yao Lin, Taipei (TW)

(73) Assignees: National Taiwan University, Taipei (TW); National Taipei University of Technology, Taipei (TW)

( * ) Notice: Subject to any disclaimer, the term of this patent is extended or adjusted under 35 U.S.C. 154(b) by 287 days.

(21) Appl. No.: 12/782,974

(22) Filed: May 19, 2010

(65) Prior Publication Data

US 2011/0288631 A1    Nov. 24, 2011

(51) Int. Cl.
*A61F 2/06* (2013.01)
*A61F 2/915* (2013.01)

(52) U.S. Cl.
CPC ....... *A61F 2/915* (2013.01); *A61F 2002/91575* (2013.01)
USPC ........................................ 623/1.15

(58) Field of Classification Search
CPC ..................... A61F 2002/91575; A61F 2/915
USPC .................................................. 623/1.11–1.54
See application file for complete search history.

(56) References Cited

U.S. PATENT DOCUMENTS

| | | | | |
|---|---|---|---|---|
| 5,776,161 | A * | 7/1998 | Globerman | 606/194 |
| 6,997,944 | B2 * | 2/2006 | Harrison et al. | 623/1.15 |
| 7,335,225 | B2 * | 2/2008 | Ley et al. | 623/1.15 |

* cited by examiner

*Primary Examiner* — David Isabella
*Assistant Examiner* — Ann Schillinger
(74) *Attorney, Agent, or Firm* — WPAT, P.C.; Anthony King; Kay Yang

(57) ABSTRACT

A novel cardiovascular stent for preventing vascular stenosis is disclosed. The basic components of the cardiovascular stent of the present invention include V-shape rib unit, multi-link unit and connective ring unit. In addition, each ring rib part is formed by a plurality of double V-shape rib units that are connected together via the bridging portions of the multi-link units. Also, each connective part comprises a plurality of connective ring units. The integrally formed stent of the present invention is formed with the ring rib parts that are connected together by the connective parts.

2 Claims, 13 Drawing Sheets

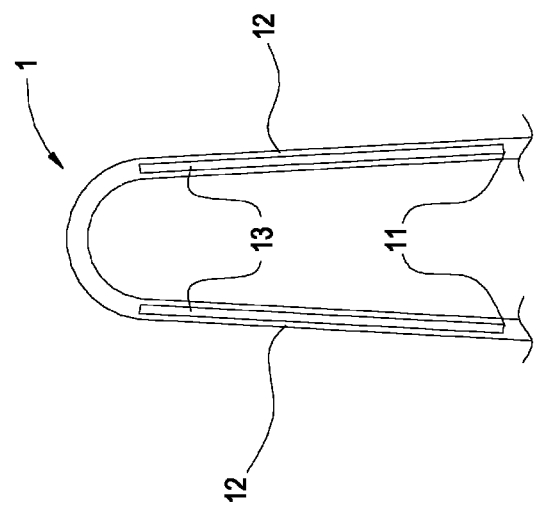
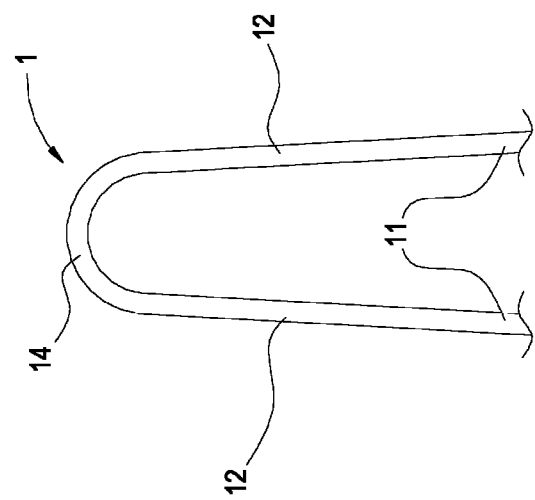

PREVENTING VASCULAR STENOSIS OF CARDIOVASCULAR STENT

BACKGROUND OF THE INVENTION

1. Field of the Invention

The invention generally relates to a novel cardiovascular stent. More particularly, the invention relates to a cardiovascular stent that can prevent vascular stenosis.

2. Description of the Prior Art

More and more people in the world are getting cardiovascular diseases and most of them have diseases associated with coronary arteries and carotid arteries. In addition, the major cause of death is the clogging and stenosis of the vessels. Balloon angioplasty and stent have been used for the treatment of such clogging and stenosis. The aim is to use the stent, which is flexible and can support the inner wall of the vessel, to prevent the recurrence of such clogging and stenosis due to the hyperplasia of the tissues.

Stent has been used for the treatment of cardiovascular diseases and is often placed inside coronary arteries and carotid arteries. Its external diameter is in the range from 2 to 10 mm and its length is in the range from 5 to 60 mm. The dimensions are determined by the actual condition. In addition, stent may also be used for bile tube, gullet tube, vein system and urethra. In installation, a stent is first guided and moved to an appropriate place by a guiding tube and then the stent is extended along with the inflated balloon so as to achieve the normal level of blood flow. However, the clogging and stenosis of the vessel may reoccur after the stent is implanted due to the reduction of the stent's flexibility or the hyperplasia of the tissues.

To reduce the recurrence of such clogging and stenosis, most of the research in the field includes the different materials (such as magnesium, titanium, cobalt and the alloy of chrome and nickel) that are used to make the stent and the use of medicine (that can suppress the growth of tissues) placed on or in the stent and radioactive treatment. In addition, the cardiovascular stent of the present invention can provide a novel cardiovascular stent that can evenly spread out the stress, provide better support and withstand a higher level of fatigue.

The novel stent of the present invention has a new application. It may be used for patients who need to undergo renal dialysis. The stent is placed inside a vessel and then a dialysis machine is connected with the vessel. In this manner, the injury to the vessel and the necrosis of tissues due to the invasive nature of the renal dialysis may be avoided or alleviated.

To eliminate the disadvantages in the prior art, the inventor has put a lot of effort into the subject and has successfully come up with the cardiovascular stent of the present invention.

SUMMARY OF THE INVENTION

An object of the present invention is to provide a novel cardiovascular stent that can prevent vascular stenosis.

Another object of the present invention is to provide a novel cardiovascular stent that has a new application for the patients who need to undergo renal dialysis.

A third object of the present invention is to provide a novel cardiovascular stent that can evenly spread out the stress, provide better support and withstand a higher level of fatigue.

To reach these objects, the cardiovascular stent of the present invention is disclosed. The cardiovascular stent of the present invention comprises a plurality of ring rib parts and a plurality of connective parts. Each ring rib part is formed by a plurality of double V-shape rib units that are connected together via the bridging portions of the multi-link units. Each connective part comprises a plurality of connective ring units. The cardiovascular stent is formed by the ring rib parts that are connected together via the connective ring units.

These features and advantages of the present invention will be fully understood and appreciated from the following detailed description of the accompanying Drawings.

BRIEF DESCRIPTION OF THE DRAWINGS

FIG. 1A is a view illustrating the V-shape rib unit of the cardiovascular stent of the present invention. FIG. 1B is another view illustrating an elongated slot (able to hold and release medicine) provided in the two legs of the V-shape rib unit.

DETAILED DESCRIPTION OF THE PREFERRED EMBODIMENT

Though a preferred embodiment will be elaborated in the following description, it should be understood that the description is to be regarded in an illustrative manner rather than a restrictive manner.

The stent of the present invention is manufactured by laser cutting and is integrally formed. The stent has a transversal net-like structure, which enables the stent to bend and extend.

The basic components of the cardiovascular stent of the present invention include V-shape rib unit, multi-link unit and connective ring unit. In the following description, we will elaborate on these components first and then on how these components are put together to form the stent of the present invention.

V-Shape Rib Unit

Figure 3:
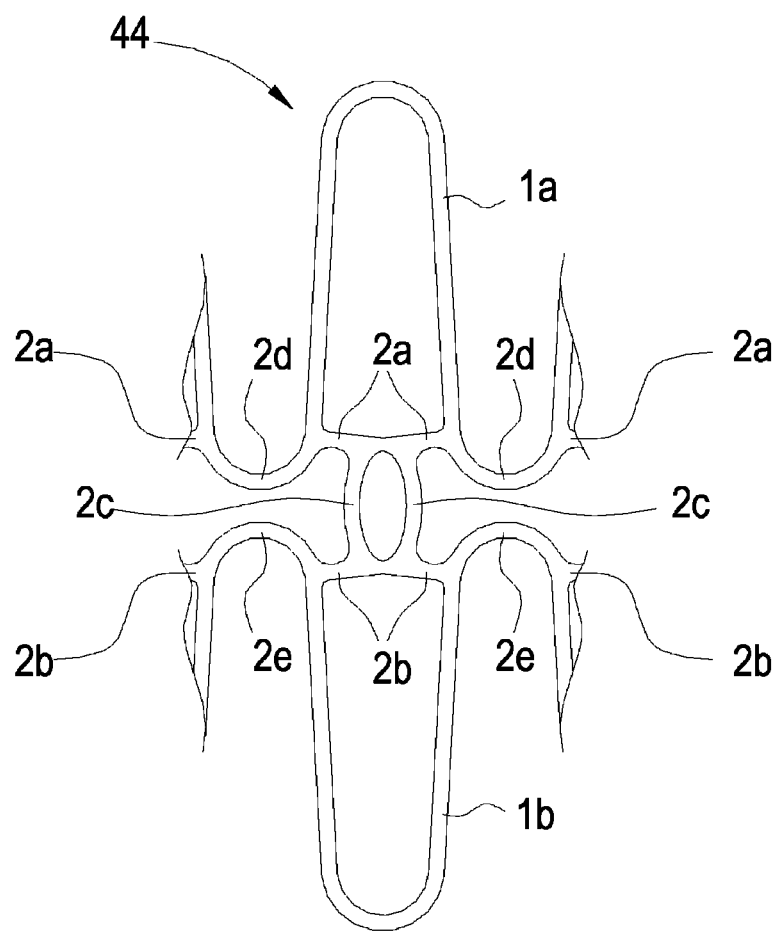
FIG. 3 is a view illustrating the double V-shape rib unit of the cardiovascular stent of the present invention.

Please see FIGS. 1A and 3, which illustrate the V-shape rib unit and double V-shape rib unit, respectively, of the cardiovascular stent of the present invention. The two ends 11 of the V-shape rib unit 1 may be connected with the first connective portion 2a or the second connective portion 2b of the multi-link unit 2. A double V-shape rib unit 44 is formed by the connection between the first V-shape rib unit 1a and the second connective portion 2a as well as the connection between the second V-shape rib unit 1b and the second connective portion 2b.

As illustrated in FIG. 1B, an elongated slot 13 may be provided in the two legs 12 of the V-shape rib unit 1 to hold and release medicine.

Each V-shape rib unit may have a V shape or a U shape or a shape between a V shape and a U shape. In addition, the top portion 14 of the V-shape rib unit 1 has a smooth, round design, instead of a sharp design, so as to avoid damages to the walls of blood vessels. In addition, the angle between the two legs is in the range from 2 to 5 degree. Therefore, the average stress level of the stent of the present invention after the inflation of the balloon is less than that of the stent of the prior art.

The aforesaid medicine includes but not limited to drugs or substances suitable to be used for the stent of the present invention, such as drugs or substances that can suppress the growth of tissues, drugs or substances that can suppress clogging, radioactive material and other drugs or substances that have therapeutic effect or are suitable for the stent of the present invention.

Multi-Link Unit

Figure 2:
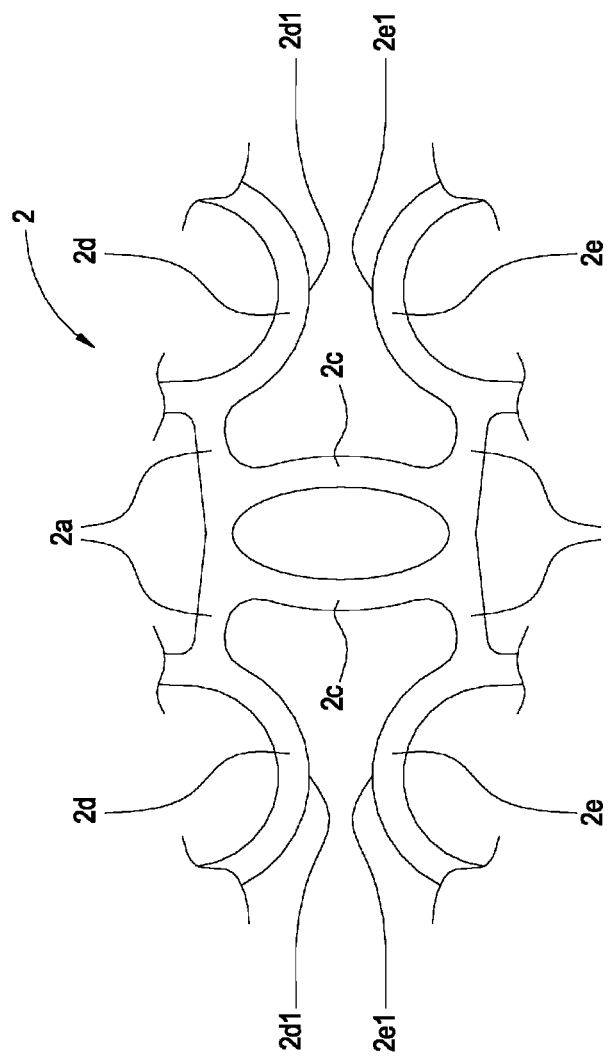
FIG. 2 is a view illustrating the multi-link unit of the cardiovascular stent of the present invention.

Please see FIG. 2, which illustrates the multi-link unit of the cardiovascular stent of the present invention. The multi-link unit 2 comprises a first connective portion 2a, a second connective portion 2b, a central oval connective portion 2c, a first bridging portion 2d and a second bridging portion 2e. The first connective portion 2a is connected with the second connective portion 2b through the central oval connective portion 2c. The central oval connective portion 2c is connected with the first bridging portion 2d through the first connective portion 2a. The central oval connective portion 2c is connected with the second bridging portion 2e through the second connective portion 2b. The multi-link unit has the properties of a spring and hence can evenly distribute stress and can enhance the extension capacities in the axial and radial directions.

The first bridging portion 2d and second bridging portion 2e may have the shape of semicircle or arc. In an embodiment, the convex surface 2d1 of the first bridging portion 2d points at the opposite direction with respect to that of the convex surface 2e1 of the second bridging portion 2e.

Double V-Shape Rib Unit

As illustrated in FIGS. 2 and 3, a double V-shape rib unit 44 is formed by the connection between a V-shape rib unit and another V-shape rib unit via the connection between the first bridging portion 2d and the first connective portion 2a as well as the connection between the second bridging portion 2e and the second connective portion 2b.

Connective Ring Unit

Figure 4:
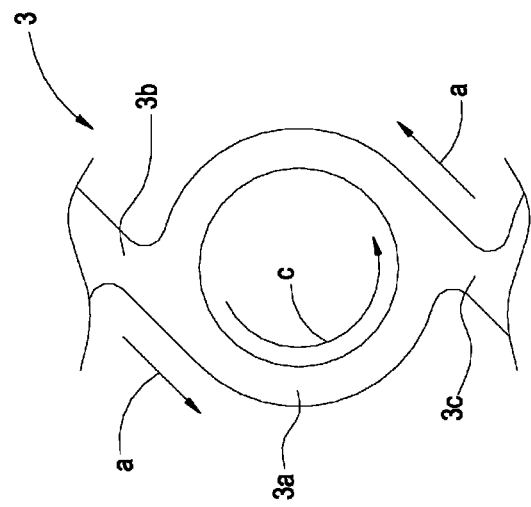
FIG. 4A is a view illustrating a clockwise connective ring unit of the cardiovascular stent of the present invention.
FIG. 4B is a view illustrating a counterclockwise connective ring unit of the cardiovascular stent of the present invention.
FIG. 4C is a view schematically illustrating how a clockwise connective ring unit connects two double V-shape rib units together.
Figure 4:
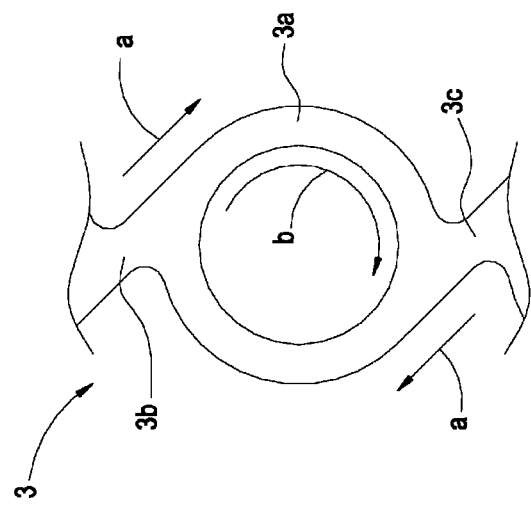
Figure 4:
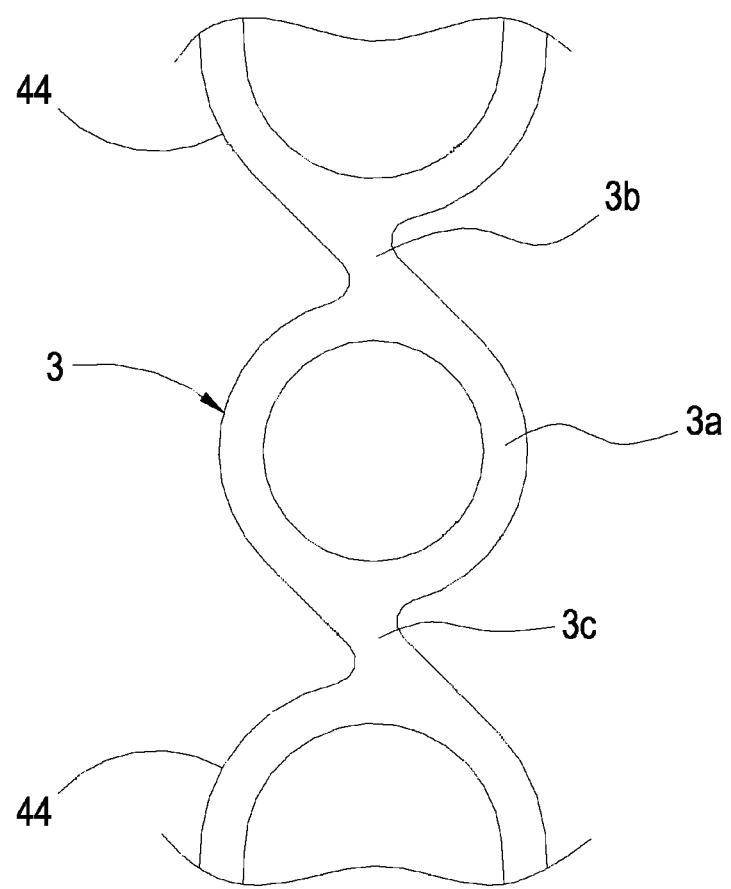

Please see FIGS. 4A, 4B and 4C, which are three views illustrating the connective ring unit of the cardiovascular stent of the present invention.

The connective ring unit 3 comprises a connective ring 3a, a first tangential connective portion 3b and a second tangential connective portion 3c. The connective ring 3a is connected with a double V-shape rib unit via the first tangential connective portion 3b and the second tangential connective portion 3c. The first tangential connective portion 3b and the second tangential connective portion 3c are tangent to or nearly tangent to (as indicated by the arrow "a") the connective ring 3a and they are parallel to each other. Therefore, the connective ring unit 3 can evenly spread out the stress and can extend in the axial and radial directions.

In addition, the connective ring unit 3 is clockwise as indicated by the arrow "b" in FIG. 4A and the connective ring unit 3 is counterclockwise as indicated by the arrow "c" in FIG. 4B.

The above description is about the basic components of the stent of the present invention. The stent of the present invention is integrally formed by laser cutting and is a hollow structure. We will elaborate on how they are connected together in the following.

The Cardiovascular Stent of the Present Invention

Figure 5:
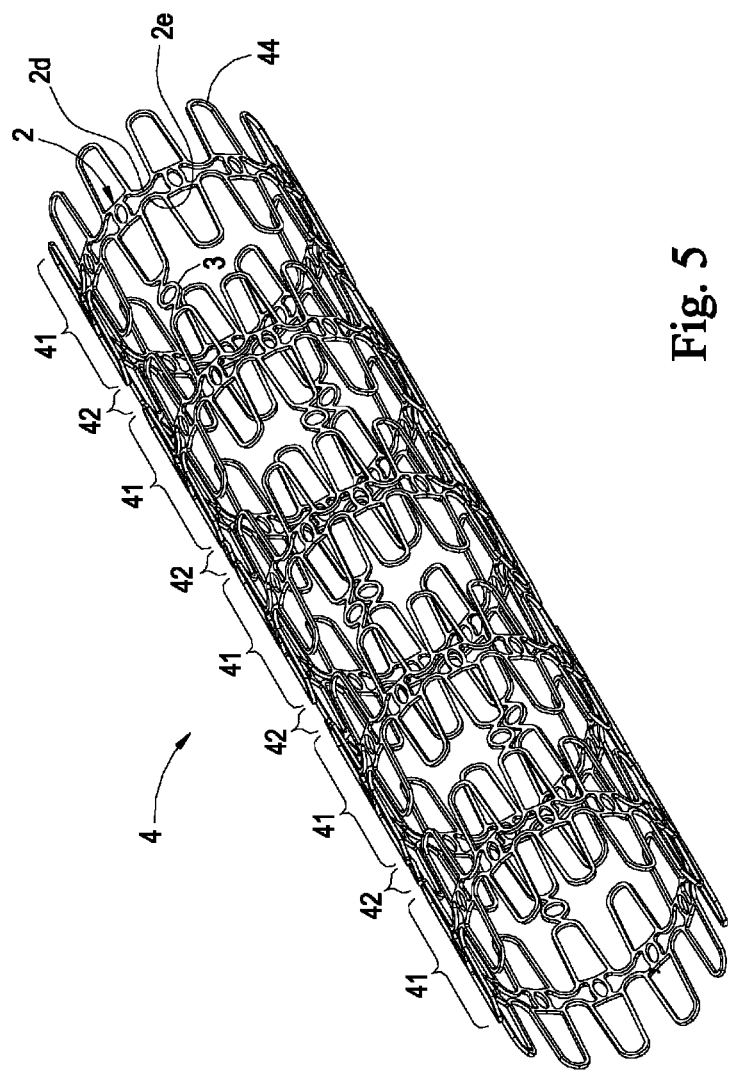
FIG. 5 is a perspective view illustrating the cardiovascular stent of the present invention.
Figure 6:
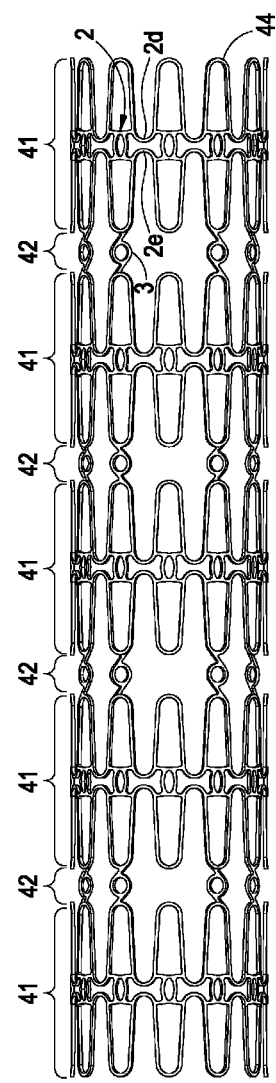
FIG. 6 is a side view illustrating the cardiovascular stent of the present invention.
Figure 7:
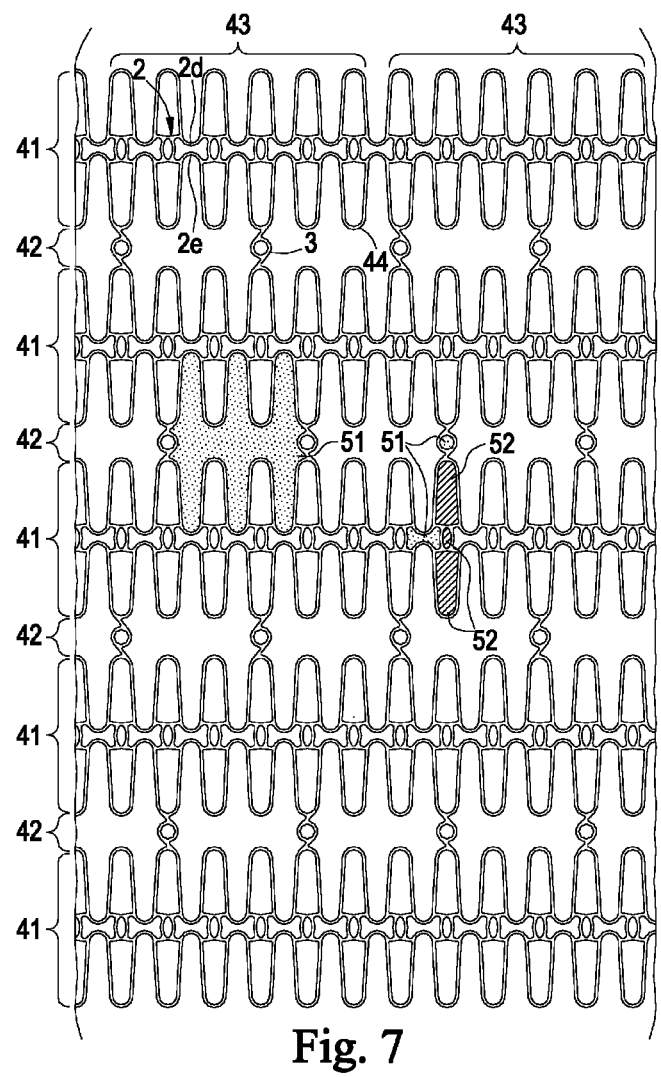
FIG. 7 is a plane developed view illustrating the cardiovascular stent of the present invention.

Please refer to FIGS. 5, 6 and 7, which are three views illustrating the cardiovascular stent of the present invention.

The cardiovascular stent of the present invention comprises a plurality of ring rib parts 41 and a plurality of connective parts 42. Each ring rib part is formed by a plurality of double V-shape rib units 44 that are connected together via the first bridging portions 2d and the second bridging portions 2e of the multi-link units 2.

Each connective part comprises a plurality of connective ring units 3.

The cardiovascular stent 4 is formed by the ring rib parts 41 that are connected together via the connective ring units 3.

The number of the ring rib parts 41 depends on the actual condition. In addition, the ring rib parts 41 may be connected together by the connective ring units 3 in an orderly configuration or a disorderly configuration.

Orderly Configuration

The orderly configuration includes but not limited to: (A) The spacing between two neighboring connective ring units 3 is "n" double V-shape rib units 44, where "n" is a positive integer (0, 1, 2, 3, 4, . . . ). When "n" equals zero, this means that a connective ring unit is used for each double V-shape rib unit 44 and, in such configuration, the stent has less flexibility. (B) All the connective ring units 3 of all the connective parts 42 are clockwise (C) All the connective ring units 3 of all the connective parts 42 are counterclockwise (D) All the clockwise and counterclockwise connective ring units 3 of all the connective parts 42 are arranged in an orderly manner (E) Though all the clockwise and counterclockwise connective ring units 3 of all the connective parts 42 are not arranged in an orderly manner, the overall structure of the stent is in an orderly configuration (as shown in FIG. 7) (F) A configuration that is a combination of "(A)" and "(B)" or other configurations that are suitable for the present invention.

Singular Stent Part

FIG. 7 illustrates a preferred embodiment of the present invention. The cardiovascular stent of the present invention is consisted of a plurality of the same singular stent parts 43 that are connected together by the first bridging portions 2d and the second bridging portions 2e of the multi-link units 2. Therefore, if we need a cardiovascular stent with a larger internal diameter, more singular stent parts are used; if we need a cardiovascular stent with a smaller internal diameter, less singular stent parts are used.

Figure 8:
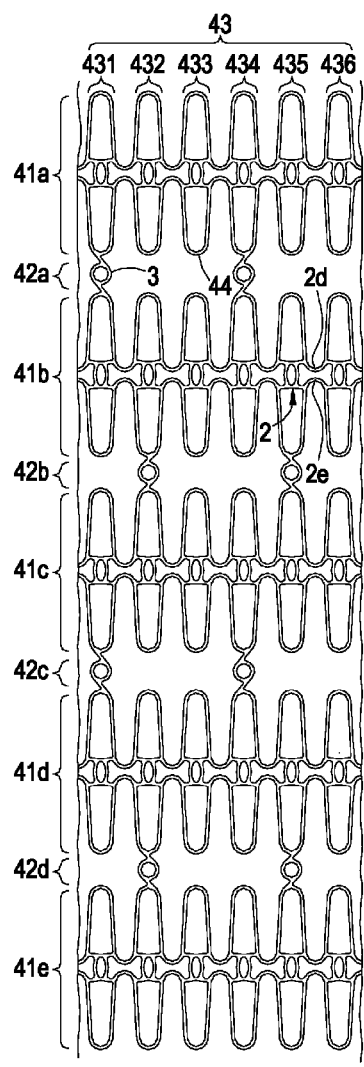
FIG. 8 is a plan developed view illustrating the double V-shape rib units of the cardiovascular stent of the present invention.

As illustrated in FIGS. 7 and 8, the singular stent parts 43 comprise five ring rib parts 41a to 41e and four connective parts 42a to 42d.

Each ring rib part 41 comprises six double V-shape rib units 44 that are connected together by the first bridging portions 2d and the second bridging portions 2e of the multi-link units 2.

Each connective part 42 comprises two connective ring unit 3. The five ring rib part 41 are connected together by the four connective parts 42 to form the singular stent parts 43.

The first double V-shape rib unit 431 of the first ring rib part 41a is connected with the second ring rib part 41b via a clockwise connective ring unit 3 of the first connective part 42a. The fourth double V-shape rib unit 434 of the first ring rib part 41a is connected with the fourth ring rib part 434 via a counterclockwise connective ring unit 3 of the first connective part 42a.

In addition, the second double V-shape rib unit 432 of the second ring rib part 41b is connected with the second double V-shape rib unit 432 of the third ring rib part 41c via a counterclockwise connective ring unit 3 of the second connective part 42b. The fifth double V-shape rib unit 435 of the second ring rib part 41b is connected with the fifth ring rib part 435 of the third ring rib part 41c via a clockwise connective ring unit 3 of the second connective part 42b.

Also, the first double V-shape rib unit 431 of the third ring rib part 41c is connected with the first double V-shape rib unit 431 of the fourth ring rib part 41d via a clockwise connective ring unit 3 of the third connective part 42c. The fourth double V-shape rib unit 434 of the third ring rib part 41c is connected with the fourth ring rib part 434 of the fourth ring rib part 41d via a counterclockwise connective ring unit 3 of the third connective part 42c.

Furthermore, the second double V-shape rib unit 432 of the fourth ring rib part 41d is connected with the second double V-shape rib unit 432 of the fifth ring rib part 41e via a clockwise connective ring unit 3 of the fourth connective part 42d. The fifth double V-shape rib unit 435 of the fourth ring rib part 41d is connected with the fifth ring rib part 435 of the fifth ring rib part 41e via a counterclockwise connective ring unit 3 of the fourth connective part 42d.

Figure 9:
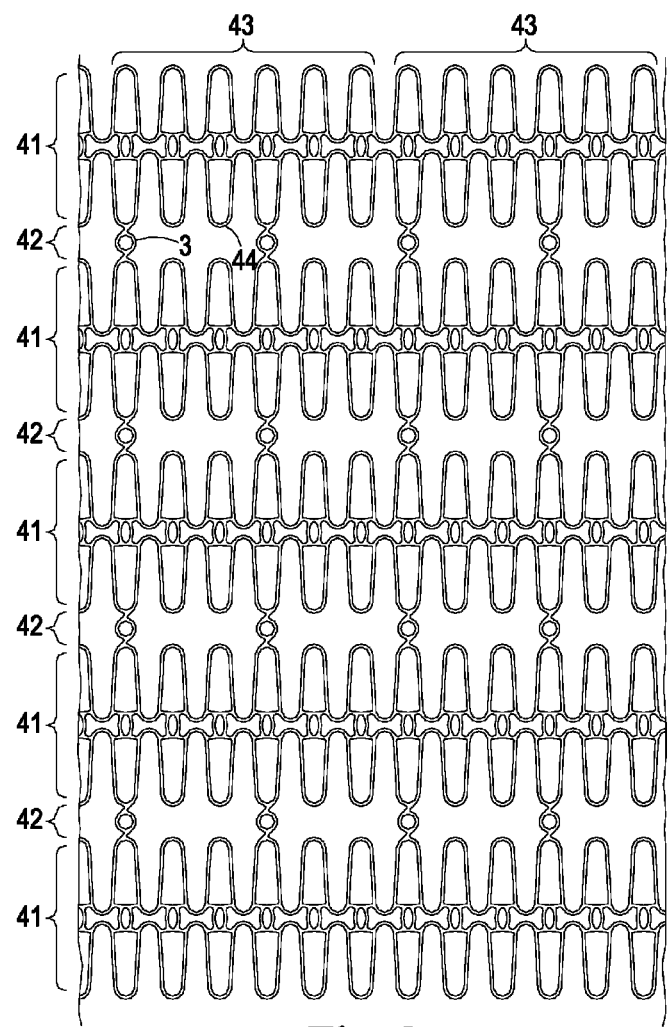
FIG. 9 is a plan developed view illustrating a cardiovascular stent of the present invention with only the counterclockwise connective ring units.

Please see FIG. 9, which illustrates another embodiment of the present invention. The ring rib parts 41 of the cardiovascular stent 4 of the present invention are connected together by the connective ring units 3 that are arranged in the same manner. In addition, only the counterclockwise connective ring units 3 are used. Each pair of counterclockwise connective ring units 3 is spaced apart by two double V-shape rib units to connect the ring rib parts 41 together.

Disorderly Configuration

The disorderly configuration includes but not limited to: (A) The connective ring units 3 are not equally spaced. The connective ring units 3 may be arranged according to the actual condition. (B) All the clockwise and counterclockwise connective ring units 3 of all the connective parts 42 are not arranged in an orderly manner and the overall structure of the stent is in a disorderly configuration. However, the end result is still a usable stent. (C) A configuration that is a combination of "(A)" and "(B)" or other disorderly configurations which are suitable for the present invention.

Open Cell Design and Closed Cell Design

There are two types of designs as determined by the shape and area of the affected region: open cell design 51 (as indicated by the dotted region in FIG. 7) and closed cell design 52 (as indicated by the region with lines in FIG. 7). The open cell design 51 has about the same area when the stent is bent; the closed cell design 52 has an area that may change when the stent is bent. The open cell design 51 can assist the passage of blood and the closed cell design may be bent after the inflation of the balloon.

Materials for Cardiovascular Stent of the Present Invention

Materials that are biocompatible and suitable for the cardiovascular stent of the present invention include but not limited to the following materials: (1) Metallic materials, such as tantalum, stainless steel (SUS 316L/LN), alloy containing cobalt, nickel and molybdenum, titanium and titanium alloy (2) Polymers, such as Teflon, HDPE and PMMA (3) Ceramic materials and composite materials (4) Biodegradable materials (5) PU for medical applications and other suitable materials. "Ceramic materials and composite materials" include: (a) Materials that do not interact with human body, such as aluminum oxide and zirconium oxide (b) Materials that interact with human body, such as phosphorite and tricalcium phosphate. "Composite materials" include two or more kinds of materials that can complement each other, such as composite carbon material and fiber-reinforced material. In "(4) Biodegradable materials", polyester material or anhydride is used to manufacture the cardiovascular stent and such stent is called biodegradable cardiovascular stent because it can degrade and disappear in human body, such as PLA (polylactic acid) and PLLA (poly L-lactide).

Figure 10:
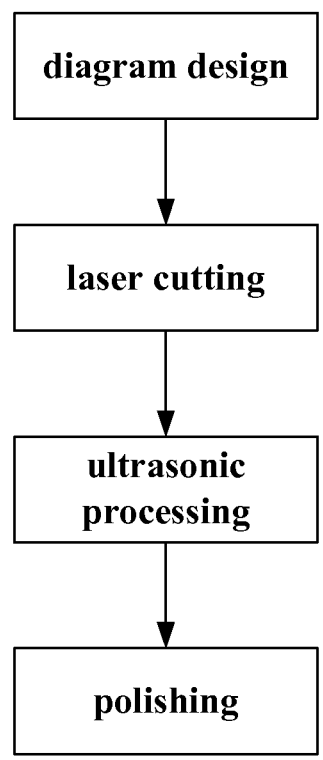
FIG. 10 is a flow chart schematically illustrating the manufacturing process of the cardiovascular stent of the present invention.

Manufacturing Process:

As illustrated by FIG. 10, the manufacturing process of the cardiovascular stent of the present invention includes but not limited to the following steps:

Step 1: Laser Cutting

Laser is used for cutting according to the diagrams of the components of the stent.

Step 2: Ultrasonic Processing

First, ultrasonic bath is used to remove the rough edges and residues generated in the laser cutting. Then, the stent is dried up. Next, the stent is submerged in an acidic solution to remove the oxides and other pollutants on the surface.

Step 3: Polishing

The rough surface of the stent may affect the performance of the stent and may cause the hyperplasia of the blood vessel intima and lower the resistance to infection. Chemical polishing or electrolysis polishing may be used to remove the rough edges and residues generated in the laser cutting and smooth out the rough surfaces in the radial direction so that the surfaces of the stent may become smooth and be free of residues.

The manufacturing process may further include smoothing step, coating and disinfecting.

Coating:

A layer of a biodegradable material containing medicine may be coated on the surfaces of the stent. After such stent is implanted into our body, the medicine may be released gradually so as to reduce the risk of the second thrombosis.

Disinfecting

First, the stent is washed because there may be chemical residues or other pollutants remaining on the stent. Then, disinfecting or sterilizing is carried out.

Medical disinfectant may be used for the disinfecting and may kill non-spore type microorganisms (may kill germs, tuberculin, funguses and viruses). Such disinfecting takes at least 20 minutes. Alcoholic solution with the concentration in the rage of 60 to 90% (v/v) (70% is the most commonly used concentration) may also be used as the disinfectant. Organic material remaining on the stent may reduce the effect of the disinfectant and is harmful to mucous membranes.

Commonly Used Germ-Killing Methods Include:

Steam at 121 Degree C.:

Such method takes 45 to 75 minutes. Such method would not pollute the environment and the container is usually quite large. The method can not be used for objects that can not withstand high temperatures or wetness and can not be used for powder type objects and oil type materials.

(2) Radioactive Radiation:

In this method, the heat and chemical energy generated in the ionization process of the gamma ray or beta ray is used to kill microorganisms by destroying their DNA. Though radioactive radiation has a strong capacity of penetration, such method is relatively expensive and requires special machines, protective gears and protective measures.

(3) Low Temperature Plasma

In this method, electric energy is applied to an activated gas in the environment of vacuum and the gas is used to kill microorganisms by destroy their metabolic function via the free radicals generated by the collision of ions and molecules. The method may be carried out under 50 degree C. and special wrapping material is required. Only oxygen and water are produced in the method and hence the method generates no pollutant. The method takes 55 to 75 minutes and is applicable to medical devices that can not withstand heat and wetness. The method is not suitable for products made of plant fibers, cloth sheets, liquids and powder type materials. The container is not large. Because such method has a relatively weak capacity of penetration, the method has limits on the diameters and lengths of objects that will undergo such method.

Surface Treatment

Because a cardiovascular stent has a direct contact with the wall of our blood vessel, its surfaces have to be smooth. After a stent undergoes process such as laser cutting or other process, it should undergo surface polishing process to smooth its surfaces.

In the prior art, surface polishing process can smooth the surfaces and provide the stent with therapeutic effect as well as enhance the capacities of the stent in oxidation resistance, corrosion resistance and bio compatibility. Surface polishing processes suitable for the stent of the present invention include but not limited to naked type, coating type, membrane type, chemical polishing and electrolysis polishing. Naked type means that the stent undergoes regular polishing only. Coating type means that the stent is coated with a thin layer of medicine to reduce the possibility of thrombosis. Membrane type means that the stent is coated with a thin layer of polymer. Chemical polishing means that suitable chemical(s) is used to polish the stent. Electrolysis polishing means that the stent undergoes laser treatments for many times or undergoes high temperature treatment.

Usage

Figure 11:
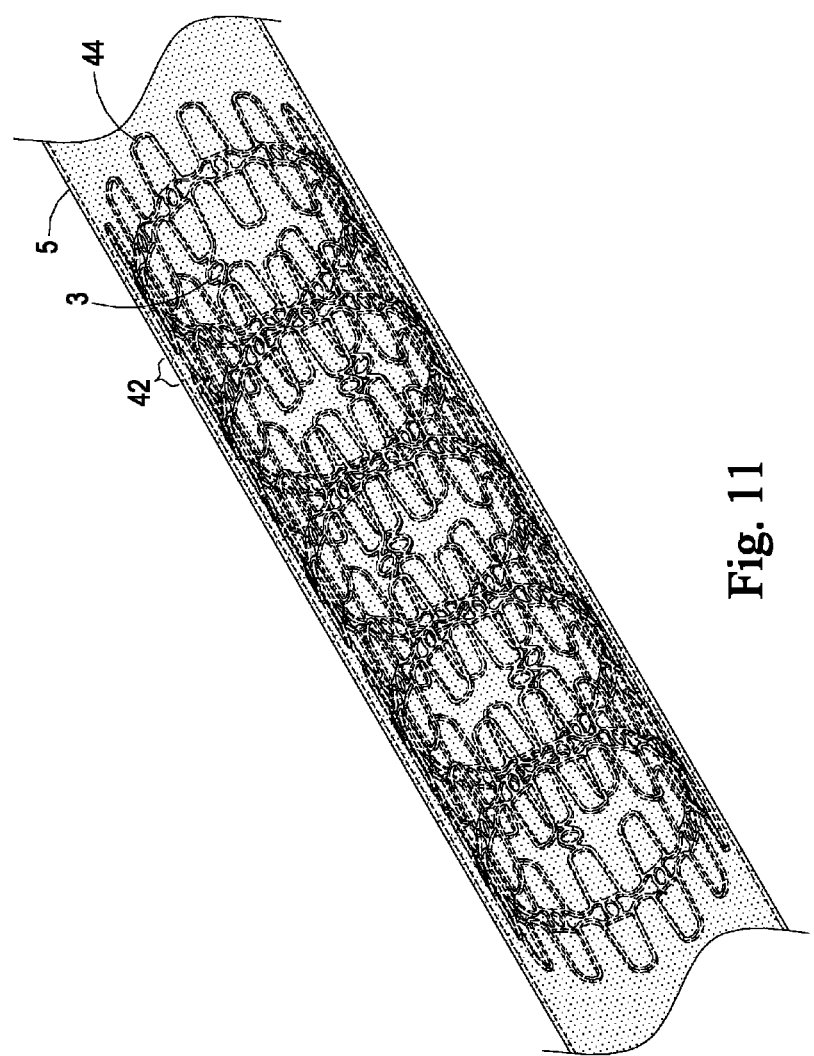
FIG. 11 is a view illustrating the stent of the present invention that has been installed on a wall inside a blood vessel.

Please see FIG. 11, which illustrates the stent 4 of the present invention that has been installed on a wall 5 inside a blood vessel. The double V-shape rib units 44 of the stent 4 can support the blood vessel. Because the connective parts 42 comprise a plurality of connective ring units 3, the stent may be bent and twisted and hence may be installed inside blood vessels that have different shapes and different curvatures.

Figure 12:
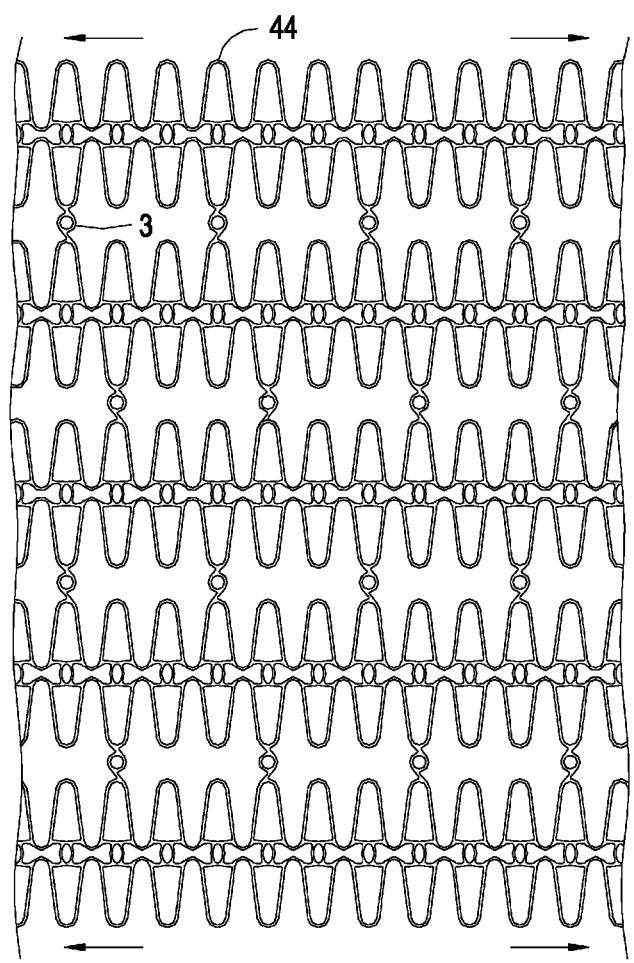
FIG. 12 is a view illustrating the stent of the present invention that has been extended by a balloon with the components pulled apart in the directions indicated by the arrows.

Please refer to FIG. 12, which illustrates the stent 4 of the present invention that has been extended by a balloon. Because the stent 4 is integrally formed and the transversal net-like structure is flexible and extendable, the components are pulled apart in the directions indicated by the arrows. For example, the distance between two connective ring units 3 becomes larger and the distance between two double V-shape rib units 44 gets bigger too. Such increase in distance may provide support to the vessel and such distance may be adjusted according to the inner diameter of a vessel. According to the relevant tests, the stent may be extended up to 2.8 to 8 mm in diameter by a balloon.

The stent of the present invention may be used for coronary arteries, carotid arteries, bile tube, gullet tube, vein system and urethra. Moreover, the novel stent of the present invention has a new application. It may be used for patients who need to undergo renal dialysis. The stent is placed inside a vessel and then a dialysis machine is connected with the vessel. In this manner, the injury to the vessel and the necrosis of tissues due to the invasive nature of the renal dialysis may be avoided or alleviated. In addition, the dimensions and diameter of the stent may be adjusted according to the actual condition, such as the actual blood clogging condition and the different inner diameters of the vessel.

In comparison to the stent of the prior art, according to the tests of the stress distribution, fatigue and supporting capacity, the stent of the present has a better stress distribution, provides better support and withstands a higher level of fatigue.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A cardiovascular stent, comprising:
   a plurality of ring rib parts, wherein each ring rib part is formed by a plurality of double V-shape rib units that are connected together via a multi-link unit; and
   a plurality of connective parts, wherein each connective part comprises a plurality of connective ring units,
   characterized in that the cardiovascular stent is formed by the ring rib parts that are connected together via the connective ring units,
   and characterized in that each double V-shape rib unit comprises a first V-shape rib unit, a second V-shape rib unit and the multi-link unit and each V-shape rib unit is formed by a connection between the first V-shape rib unit and the first connective portion of the multi-link unit as well as the connection between the second V-shape rib unit and the second connective portion of the multi-link unit,
   wherein the multi-link unit further includes a first bridging portion and a second bridging portion and the first bridging portion and the second bridging portion have the shape of semicircle or arc, wherein the convex surface of the first bridging portion points at the opposite direction with respect to that of the convex surface of the second bridging portion,
   wherein each multi-link unit comprises a first connective portion, a second connective portion, a central oval connective portion, the first bridging portion and the second bridging portion, and wherein the first connective portion is connected with the second connective portion through the central oval connective portion and the central oval connective portion is connected with the first bridging portion through the first connective portion, and wherein the central oval connective portion is connected with the second bridging portion through the second connective portion,
   wherein the multi-link unit has the properties of a spring that evenly distribute stress and enhance extension capacities in the axial and radial directions;
   wherein the connective ring unit comprises a connective ring, a first tangential connective portion and a second tangential connective portion and the connective ring is connected with a double V-shape rib unit via the first tangential connective portion and the second tangential connective portion, and wherein the first tangential connective portion and the second tangential connective portion are tangent to or nearly tangent to the connective ring and they are parallel to each other, wherein each of the connective ring units is disposed in an opposite direction to the one adjacent to it to form an asymmetrical design.

2. The cardiovascular stent as in claim 1, wherein each V-shape rib unit may have a U shape or a shape between a V shape and a U shape.

* * * * *